(12) United States Patent
Bockelmann et al.

(10) Patent No.: US 7,763,733 B2
(45) Date of Patent: Jul. 27, 2010

(54) RITONAVIR ANALOGOUS COMPOUND USEFUL AS RETROVIRAL PROTEASE INHIBITOR, PREPARATION OF THE RITONAVIR ANALOGOUS COMPOUND AND PHARMACEUTICAL COMPOSITION FOR THE RITONAVIR ANALOGOUS COMPOUND

(75) Inventors: Maria Alice Bockelmann, Itapira (BR); Simone Soares Rosatto, Itapira (BR); Cláudio Roberto Fuzeto, Itapira (BR); Thiago Boscaro Vernucci, Itapira (BR); Daniela Cecília Barel, Campinas (BR); Kesley Moraes Godinho de Oliveira, Itapira (BR); Matheus Puginna de Freitas, Itapira (BR)

(73) Assignee: Cristalia Produtos Quimicos Farmaceuticos Ltda., Itapira, SP (BR)

( * ) Notice: Subject to any disclaimer, the term of this patent is extended or adjusted under 35 U.S.C. 154(b) by 797 days.

(21) Appl. No.: 11/596,469

(22) PCT Filed: May 11, 2005

(86) PCT No.: PCT/BR2005/000077
§ 371 (c)(1),
(2), (4) Date: Feb. 2, 2007

(87) PCT Pub. No.: WO2005/008977
PCT Pub. Date: Nov. 17, 2005

(65) Prior Publication Data
US 2007/0244168 A1    Oct. 18, 2007

(30) Foreign Application Priority Data
May 13, 2004  (BR) .................... 0401742

(51) Int. Cl.
*A61K 31/427* (2006.01)
*C07D 417/12* (2006.01)
(52) U.S. Cl. .................... 548/204; 514/365
(58) Field of Classification Search ............ 548/204
See application file for complete search history.

(56) References Cited

U.S. PATENT DOCUMENTS 5,541,206 A    7/1996   Kempf et al.
5,567,823 A   10/1996   Tien et al.

OTHER PUBLICATIONS

Huff, Journal of Medicinal Chemistry, 34(8) 1991, pp. 2305-2314.*

* cited by examiner

*Primary Examiner*—Laura L. Stockton
(74) *Attorney, Agent, or Firm*—Birch, Stewart, Kolasch & Birch, LLP

(57) ABSTRACT

The present invention describes a new one ritonavir analogous compound that presents significantly superior activity in inhibition of HIV protease. There are also described the usage of the ritonavir analogous compound of the present invention or salt, ester or prodrug thereof as well as the usage of the compound and its pharmaceutical compositions in medicine, particularly, in the treatment of HIV infection, by itself or in combination with others anti-HIV drugs.

6 Claims, 2 Drawing Sheets

| Structural Formula Example | EC$_{50}$ (μM) |
|---|---|
|  Example 1C | 0.0005 |
|  Example 3C | 2.0 |
|  Example 2 | 0.50 |
|  Ritonavir (Control) | 0.038 |

RITONAVIR ANALOGOUS COMPOUND USEFUL AS RETROVIRAL PROTEASE INHIBITOR, PREPARATION OF THE RITONAVIR ANALOGOUS COMPOUND AND PHARMACEUTICAL COMPOSITION FOR THE RITONAVIR ANALOGOUS COMPOUND

BACKGROUND OF THE INVENTION

The present invention refers to a new HIV protease inhibitor compound or salt or prodrug or ester thereof, to the preparation process for this new compound, pharmaceutical composition thereof and therapeutic use of such compound.

Particularly, the compound of the present invention that is a ritonavir analog, has activity for inhibiting HIV protease, an essential enzyme involved in HIV replication process, as shown hereinafter. Consequently, the compound of this invention can be used in HIV infection treatment, itself or in combination with other anti-HIV medicaments.

Human Immunodeficiency Virus (HIV) is a retrovirus (constituted by RNA) belonging to the Lentivirinae subfamily, capable to impair the human immunologic system causing the infectious disease known by the acronym AIDS (Acquired Immuno Deficiency Syndrome) [Pecanha, E. P.; Antunes, O. A. C; Tanuri, A.; Quim Nova, Vol. 25, No. 6B, 1108-1116, 2002].

HIV genome has three main regions: the gag region that codifies inner structural proteins p17, p24, p7 and p6; the pol region that codifies the protease (p11, PR), reverse transcriptase (p66/p51, RT) and the integrase (p31, IN/and, finally the env region, encoding the coating proteins, qp120 and gp41. The HIV-1 genome further encodes six other accessory proteins, wherein two of them (tat and rev) function in regulation of gene expression [Frankel, A. D.; Young, J. A. T.; *Annu. Rev. Biochem.* 67, 1, 1998].

Cellular infection occurs when HIV virus binds to a cellular receptor, generally the T-cell $CD4^+$ receptor, by means of the gp120 protein; then, virus merges with the cell membrane and the capsid content is released into the cell cytoplasm. The HIV enzyme, reverse transcriptase, catalyses DNA copy production starting from HIV virus RNA. The double helix DNA copy is then transported to the cellular nucleus where a second HIV enzyme, the integrase, catalyses the incorporation of viral DNA to the host genetic material. Subsequent viral gene expression results in RNA transcription starting from HIV DNA and in translation of viral proteins.

However, newly formed viral proteins are produced in the form of polyprotein precursors that are long entities consisting of viral enzymes and structural proteins added to each other. Polyproteins and viral RNA move to the cell surface where they are incorporated into the new viruses that spring from cell membrane taking part of it with them to form the external layer of the viruses.

Newly formed viruses, however, cannot be infectious without the action of a third essential HIV enzyme, the protease, that turns viral polyproteins into functional and structural proteins and enzymes [Nora de Souza, M. V.; Almeida, M. V.; *Quim. Nova*, Vol. 26, No. 3, 366-373, 2003].

Proteases are enzymes that cleave others proteins at highly specific sites. HIV protease, an aspartyl protease, cleaves viral polyproteins into essential functional proteins during the process of maturation of the "virion" (complete viral particle). This process occurs when each new "virion" springs outside of the infected cell membrane and it continues after the release of immature virus by the cell.

If polyproteins are not cleaved, virus formation does not finish and it becomes unable to infect a new cell. Protease inhibitors, as this name implies, are substances able to inhibit protease enzyme function. They perform their inhibitory effect disabling the enzyme before it cleaves gag/pol polyprotein to form its essential products.

The HIV genome codifies protein precursors known as gag and gag-pol that are processed by viral protease to obtain the protease, reverse transcriptase, integrase and structural proteins of the virus nucleus. Many studies were and still are dedicated to HIV control by the inhibition of the viral coded enzymes. Compounds available nowadays as anti-HIV drugs are capable of inhibiting different phases of viral replication, being classified according to the viral enzymes that they inhibit. They are distributed in three categories: nucleoside-nucleotide reverse transcriptase inhibitors (NRTIs), non-nucleoside reverse transcriptase inhibitors (NNRTIs) and protease inhibitors (PIs).

Particularly, many studies have been dedicated to the inhibition of HIV protease and the protease inhibitors saquinavir, indinavir, ritonavir, nelfinavir, amprenavir and lopinavir are examples of compounds of this category that have been approved by north-American agency of pharmaceutical products control, FDA ("Food and Drug Administration"), for the treatment of HIV infection. Due to resistant strains appearing during monotherapy, the actual treatment of patients includes usage of such protease inhibitors in combination with reverse transcriptase inhibitors. Antiretroviral formulations are commercially available for each agent individually or in the form of combinations of antiretroviral agents.

Although anti-HIV drugs are already available to patients, they are not totally efficient for the disease treatment and/or reversion and many drugs used nowadays for AIDS treatment cause adverse side effects including low platelet count, renal toxicity and bone marrow cytopenia. These factors added to viral resistance to available anti-HIV therapy, demonstrate the necessity of development of new and efficient target-enzyme inhibitors, as well as drugs that act in others stages of viral replication cycle.

One of the requirements for a drug to be considered suitable for a therapeutic use is its therapeutic efficacy. So, to achieve such requirement, the drug should present adequate characteristics of bioabsorption and bioavailability.

Protease inhibitors are high molecular weight substances, normally have lipophilic character, low water solubility and, normally present low absorption and low bioavailability when therapeutically administered in a solid state. Therefore, the development of concentrated pharmaceutical compositions for the administration of these drugs is very difficult and, in addition, high and frequent doses of these substances are necessary to maintain the therapeutic level of the drug inside the body.

The protease inhibitor compound ritonavir (CAS N° 155213-67-5), which chemical name is (2S,3S,5S)-5-[N—[N—[[N-methyl-N-[(2-isopropyl-4-thiazolyl)methyl] amino]carbonyl]vanilyl]amino-2-[N [(5-thiazolyl)methoxy-carbonyl]amino-1,6-diphenyl-3-hydroxyhexane, is disclosed in PCT document number WO 94/14436 (Kempf, D. J.), as well as several analogous compounds thereof.

Ritonavir presents polymorphism, having a marked difference of solubility between each polymorph. Such characteristic was responsible for discontinuing the first commercial composition in which, along the years, started to present an increasing amount of ritonavir in the form of the less soluble polymorph crystal. Such occurrence harmed the efficacy of HIV suppression of this medicament. Two polymorphs known as polymorph I and polymorph II are disclosed in PCT document WO 00/04016.

As ritonavir presented polymorphic forms with different physical-chemical properties, a new composition, in the form of soft gelatin capsules that suppressed considerably the crystallization of less soluble polymorph, was developed. Such composition, disclosed in document WO 98/22106, is the actual available pharmaceutical composition of ritonavir in the market. However, this composition still presents some disadvantages such as reduced physical-chemical stability, low concentration of ritonavir in each capsule, and very bulky size of the capsules.

In the actual therapy, ritonavir in its commercial pharmaceutical composition in the form of soft gelatin capsules should be administered at a daily dose of 1200 mg, divided in two administrations of 600 mg each. Soft gelatin capsules commercially available contain ritonavir in an amount of 100 mg per capsule. Therefore, a patient in therapy should ingest a total of 12 capsules daily.

Use of ritonavir to inhibit an HIV infection is disclosed in U.S. Pat. No. 5,541,206 (Kempf, D. J.). Use of ritonavir in combination of one or more reverse transcriptase inhibitors to suppress an HIV infection is disclosed in the U.S. Pat. No. 5,635,523 (Kempf, D. J.). Use of ritonavir in combination with one or more HIV protease inhibitors to suppress an HIV infection is disclosed in the U.S. Pat. No. 5,674,882 (Kempf, D. J.).

In the search for new and better anti-HIV drugs, compounds designated as analogous or derivatives of protease inhibitors already approved are commonly found in the literature.

U.S. Pat. No. 5,354,866 (Kempf, D. J.) describes compounds having 1,6-diphenyl-3-hydroxyhexane group in their structure. Such ritonavir derivative compounds include, for instance, the compounds A-83962, A-81525, and A-80987, whose structures are represented below:

wherein, Ph represents a phenyl group.

In other words, this document presents the compound A-83962 in which just the 5-thiazolyl group of the ritonavir is substituted by a 3-pyridinyl group; the compound A-81525 in which (2-isopropyl-4-thiazolyl)-CH$_2$—N(CH$_3$) group of the ritonavir is substituted by the 2-pyridinyl-CH$_2$—O group; and the compound A-80987 in which, compared to ritonavir, the substituted groups in C2 and C5 of the 1,6-diphenyl-3-hydroxyhexane group are inverted, the 5-thiazolyl group is substituted by 3-pyridinyl and the (2-isopropyl-4-thiazolyl)-CH$_2$—N(CH$_3$) group is substituted by 2-pyridinyl-CH$_2$—O.

U.S. Pat. No. 5,541,206 (Kempf, D. J.) refers to retroviral protease inhibitors compounds having a general formula I:

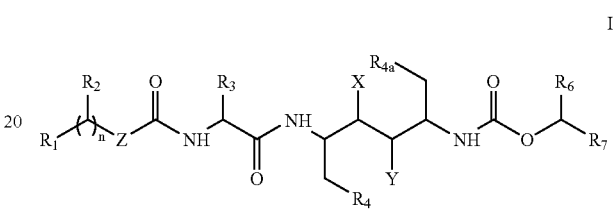

This patent describes substituent groups for each X, Y and R$_1$-R$_7$ radical of formula I and provides examples of combination among the substituents resulting in different compounds, including the protease inhibitor ritonavir (Example 1U, IC$_{50}$=0.025-0.040 μM) whose structural formula is represented below:

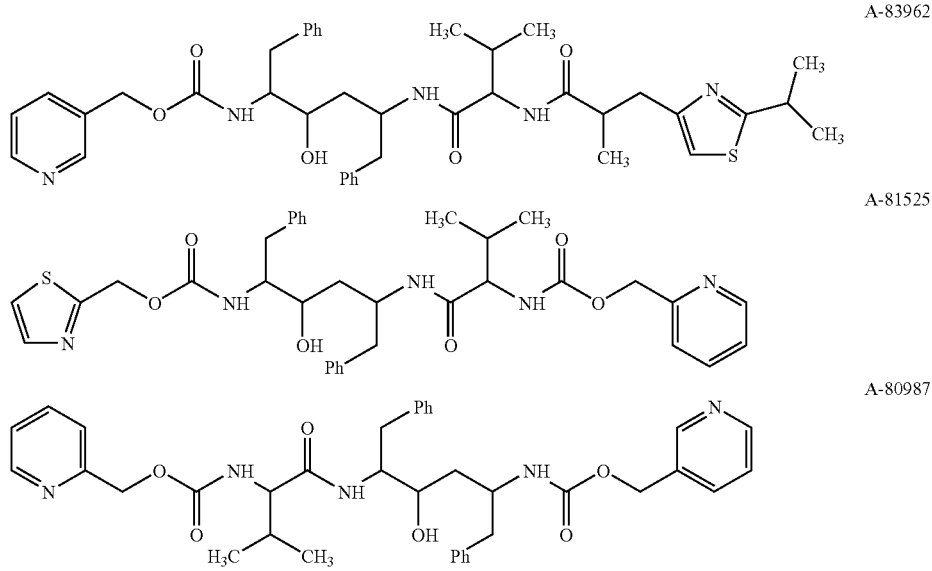

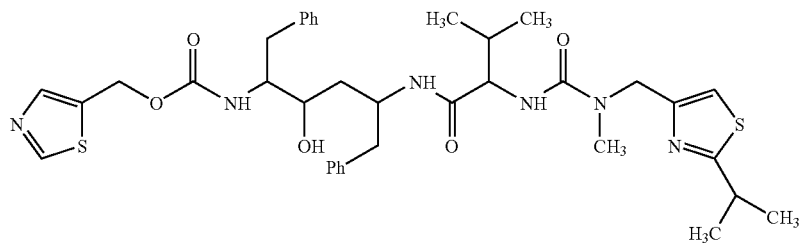

wherein Ph represents a phenyl group. Simple alterations or substituent group additions to the formula I, exemplified by ritonavir, result in different compounds that respond in different ways to the anti-HIV activity test. For instance, the addition of a 2-isopropyl substituent to the 5-thiazolyl ring of ritonavir practically does not alter $IC_{50}$ value (example 45C, $IC_{50}$=0.036-0.040 μM), however the substitution of the 2-isopropyl group by 2-isobutyl group at the 4-thiazolyl ring of ritonavir causes a significant increase of the $IC_{50}$ value (example 59G, $IC_{50}$=0.11-0.13 μM), in other words the anti-HIV activity decreases. The general formula I does not foresee "(2S,3S,5S)-2,5-Bis-substituted-1,6-diphenyl-3-hydroxyhexane" compounds.

U.S. Pat. No. 5,648,497 (Kempf D. J.) refers to retroviral inhibitor compounds of formula A-X—B, including ritonavir. Among a list of possible variations for X, the formula A-X—B that includes ritonavir and related compounds (having 1,6-diphenyl-3-hydroxyhexane group in their structure), is shown below in a simplified form represented by formula II:

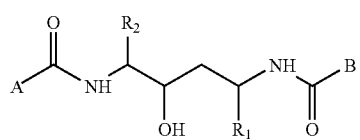

Wherein, for ritonavir:
$R_1$ and $R_2$ are —$CH_2$Ph (Ph is a phenyl group);
A is 5-thiazolyl-$CH_2$—O; and
B is —CH (isopropyl)-NH—C(O)—N($CH_3$)—$CH_2$-(2-isopropyl-4-thiazolyl)

This patent also describes compounds of formula II in which substituents A-C(O)—NH— and B—C(O)—NH— bonded at C2 and C5, respectively, are inverted in relation to ritonavir. For instance, the compound claimed in this patent wherein A is —CH(isopropyl)-NH—C(O)—N($CH_3$)—$CH_2$-(2-amino-thiazolyl) and B is 5-thiazolyl-$CH_2$—O, is represented below:

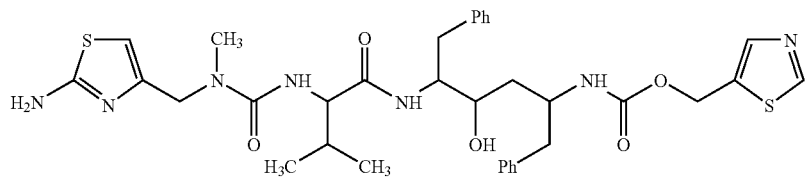

wherein Ph represents a phenyl group. Besides the compounds wherein the substituents A and B in the formula II are inverted, there are also described compounds wherein the substituents A and B are the same, e.g. the compound of the example 79 wherein A=B=(2-methyl-5-thiazolyl)-$CH_2$—O— whose structural molecular formula is shown below:

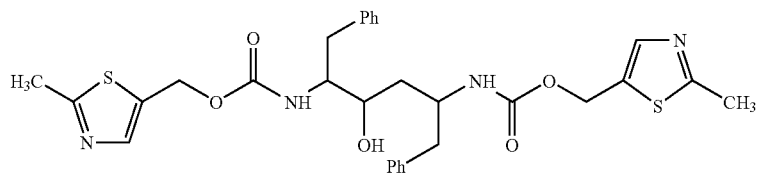

wherein Ph represents a phenyl group.

Although there are many compounds proved as protease inhibitors or potential inhibitors protected by patents and these documents generally include several variants of these compounds, the knowledge about them and the increasing scientific development can always open possibilities for the investigation and creation of new compounds. As for all new compounds, testing about various aspects from synthesis viability pre-clinical and clinical studies is necessary. There are not complete references in the literature about antiviral activity of several analogous compounds of ritonavir in which were performed the substitution of A group for B group or B group for A group, or still, wherein A group and B group are the same.

Although some 2,5-bis or -di substituted were foreseen in the literature in a generic way, they were not synthesized and/or tested for HIV protease inhibition activity.

DESCRIPTION OF THE INVENTION

Surprisingly, we verified in the present invention that some analogous compounds of ritonavir wherein A and B are the same, that is 2,5-bis or -di substituted, presented an anti-HIV activity profile very superior than the ritonavir profile and, therefore, they are interesting for HIV infection treatment.

The aim of the present invention is to propose a new analogous compound of ritonavir as well as a process for the preparation thereof. An analogous compound of ritonavir according to the present invention has the structural formula represented by formula II containing the nucleus 1,6-diphenyl-3-hydroxyhexane.

It is also an objective of the present invention to show that the new compound presents HIV protease inhibition activity and can be used in HIV infection treatment alone or in combination with other anti-HIV drugs.

The present invention describes the compound or a pharmaceutically acceptable salt, ester or prodrug thereof, having the structural formula:

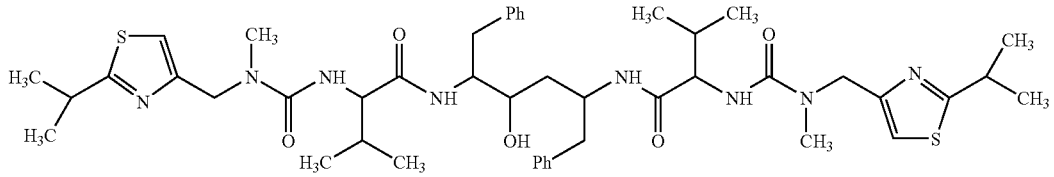

wherein Ph represents a phenyl group.

The compound of the present invention contains carbon atoms asymmetrically substituted. So, all stereoisomeric forms of the compound including racemic mixtures, diastereoisomeric mixtures and isolated diastereoisomers thereof are within the scope of the present invention.

A preferred compound of the present invention is the one that the configuration of the carbon atom beside -benzyl is "S" (C2 and C5 of 1,6-diphenyl-3-hydroxyhexane) and the configuration of the carbon atom bonded to the hydroxyl group is "S". The term configuration "S" as used herein is that defined by IUPAC [G. P. Moss *Pure and Applied Chemistry*, 68, 2193-2222 (1996)]. The valine amino acid is preferably the natural L isomer.

A preferred compound according to the present invention is (2S,3S,5S)-2, -5 bis-[N—[N—[[N-methyl-N-[(2-isopropyl-4-thiazolyl)methyl]amino]carbonyl]vanilyl]amino-1,6-diphenyl-3-hydroxyhexane or a pharmaceutically acceptable salt, ester or prodrug thereof.

Figure 1:
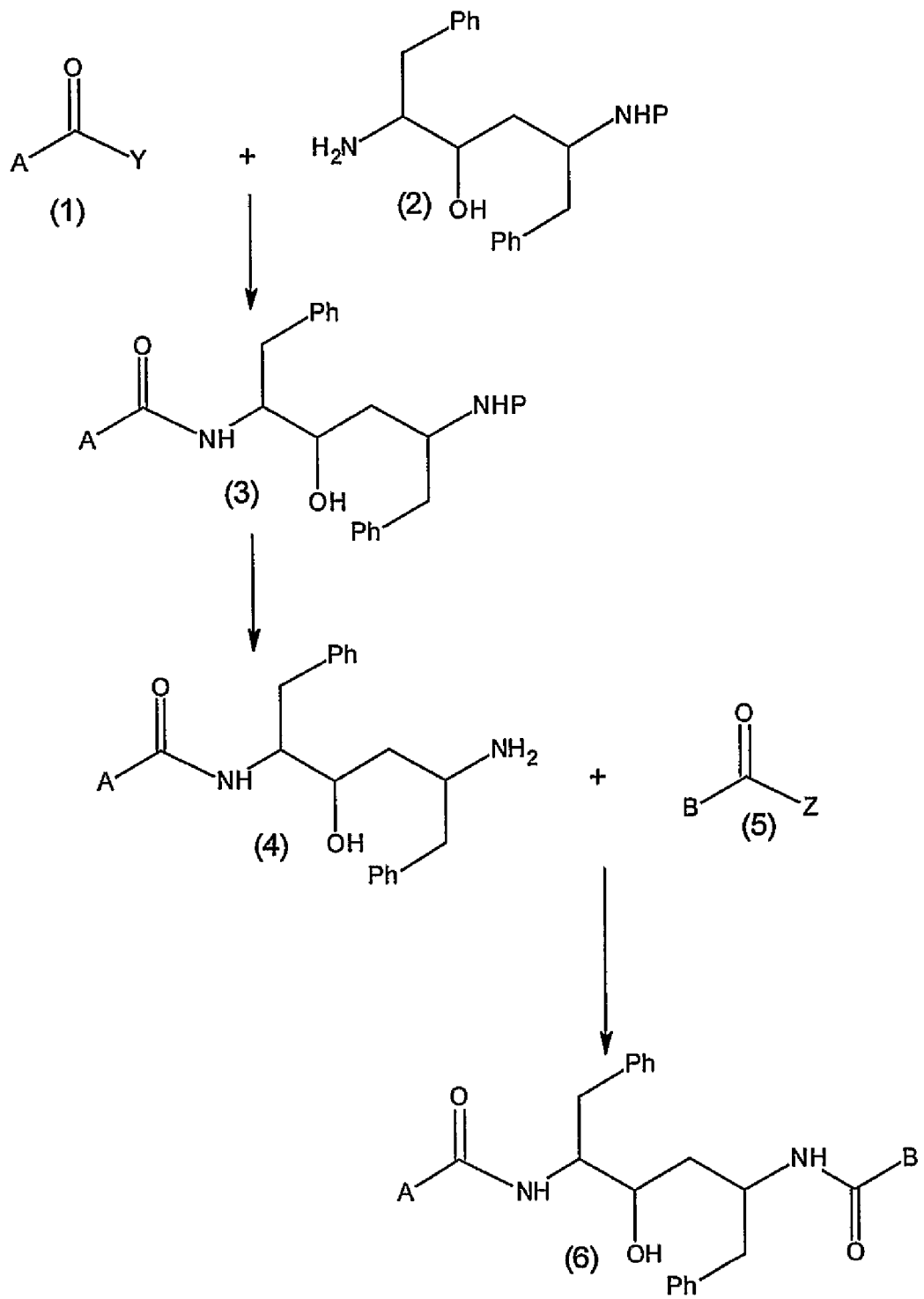
FIG. 1 illustrates a scheme for synthesis of the compounds of the invention.

The compound of the present invention can be prepared by methods known in the art as exemplified in FIG. 1. In a general way, the compound (4) can be obtained by coupling the compound (1) and (2), wherein Y can be OH or an activated ester group and P is an N-protective group, forming (3), followed by N-deprotection. Finally the compound (4) is coupled to the compound (5) wherein Z can be OH or an activated ester group to provide the analogous compound (6). For instance, the compound (4) can be obtained according to the process described in U.S. Pat. No. 5,914,332 (Sham, H. L.) by the reaction of (1, Y═OH) and (2) (P is a protective group, preferably t-butyloxycarbonyl) using tetrahydrofuran (THF) as solvent in the presence of hydroxybenzotriazol (HOBT) and dichlorohexylcarbodiimide (DCC) leading to formation of the compound (3). At the next step, the compound (3) in the presence of trifluoroacetic acid ($CF_3COOH$) and dichloromethane ($CH_2Cl_2$) is N-deprotected resulting in formation of the compound (4). The compound (4) is submitted to reaction with the compound (5, Z═OH) using tetrahydrofuran (THF) as solvent in the presence of hydroxybenzotriazol (HOBT) and dichlorohexylcarbodiimide (DCC) to provide the desired analogous compound (6).

According to the present invention the term "N-protective" as used herein refers to groups used to protect nitrogen of an amine group against undesirable reactions during synthetic process. N-protective groups commonly used are disclosed in Greene, "Protective Groups in Organic Synthesis" (John Wiley & Sons, New York, 1991) incorporated herein by reference. N-protective groups comprise acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chloro-benzoyl, 4-bromobenzoyl, 4-nitrobenzoyl and others; sulfonyl groups such as benzenesulfonyl, p-toluenesulfonyl and others; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenyl)-1-methylethoxylcarbonyl, α,α-dimethyl-3,5-dimethoxybenzyloxycarbonyl, benzhydryloxycarbonyl, t-butyl-oxycarbonyl, diisopropylmethoxycarbonyl, isopropyloxy-carbonyl, ethoxycarbonyl, methoxycarbonyl, allyloxycarbonyl, 2,2,2-trichloroethoxycarbonyl, fluorenyl-9-methoxycarbonyl, phenylthiocarbonyl, cyclopentyloxycarbonyl, adamantyloxycarbonyl, cyclohexyloxycarbonyl and others; alkyl groups such as benzyl, triphenylmethyl, benzylmethyl and others; silyl groups such as trimethylsilyl and others. Preferred N-protective groups are formyl, acetyl, benzoyl, pivaloyl, t-butylacetyl, phenylsulfonyl, benzyl, t-butyloxycarbonyl (Boc) and benzyloxycarbonyl (Cbz).

According to the present invention, the term "activated ester group" as used herein is related to acid halides such as acid chloride and activated esters including but not limited to acetic and formic acid derived anhydrides, anhydrides derived from alkoxycarbonyl halides such as isobutyloxycarbonyl chloride and others; N-hydroxysuccinimide derived esters, N-hydroxyphtalimide derived esters, N-hydroxybenzotriazol derived esters, N-hydroxy-5-norbonene-2,3-dicarboxamide derived esters, 2,4,5-trichlorophenol derived esters and others.

In order to compare the anti-HIV activity, other analogous compound of ritonavir of formula II were prepared wherein A and B are the same for one of them and A is different from B for the other compound, using the reaction scheme of FIG. 1 adapted for each case. Selected compound were:

a) A=B

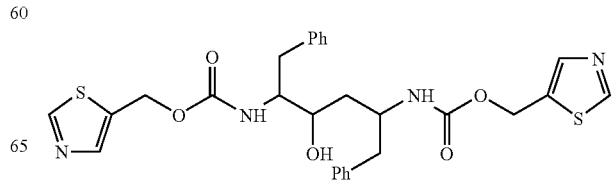

b) A≠B

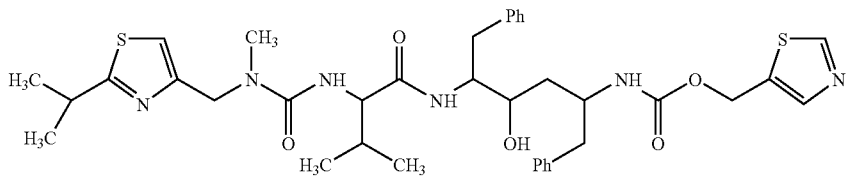

The follow examples presented hereinafter illustrate the preparation of the new compounds, as well as activity tests of HIV protease inhibition, according to the present invention.

Example 1

Preparation of the compound (2S,3S,5S)-2,5-bis-[N—[N—[[N-methyl-N-[(2-isopropyl-4-thiazolyl) methyl amino]carbonyl]valinyl]amino-1,6-diphenyl-3-hydroxyhexane A. (2S,3S,5S)-2-[N—[N [[N-methyl-N[(2-isopropyl-4-thiazolyl)methyl]amino]carbonyl]vanilyl]amino]-5-(t-butyloxycarbonylamine)-1,6-diphenyl-3-hydroxyhexane In a 6.0 L round flask equipped with stirrer system and under $N_2$ atmosphere, add (2S,3S,5S)-2-amino-3-hydroxyl-5-(t-butyloxycarbonylamine)-1,6-diphenyl hexane (100 g, 0.26 mol) and chloroform (1.9 L). After complete dissolution of the solids add a solution of N—[[N-methyl-N-[(2-isopropyl-4-thiazolyl)methyl]amino]carbonyl]L-vanilyl hydroxysuccinimide ester (107 g, 0.26 mol) in chloroform (630 mL). Monitor the reaction by thin layer chromatography and at the end of the reaction add a 10% sodium carbonate solution (1.9 L). Separate the phases and use the organic phase without previous purification directly in the next step.

B. (2S,3S,5S)-2-[N—[N—[[N-methyl-N-[(2-isopropyl-4-thiazolyl)methyl]amino]carbonyl]valinyl]amino]-5-amino-1,6-diphenyl-3-hydroxyhexane In a 6.0 L reactor equipped with addition funnel and stirrer system, add the solution obtained in the example 1A (~2.5 L) and trifluoroacetic acid (62.8 mL, 0.82 mol) slowly. Keep the system under stirring monitoring the reaction by thin layer chromatograph (TLC). After the reaction is completed add slowly a sodium carbonate solution (10%, pH=7.0). Separate the phases and dry the organic phase with sodium sulfate, concentrate it under reduced pressure and employ the crude product directly in the next step without previous purification.

C. (2S,3S,5S)-2,5-bis-[N—[N—[[N-methyl-N-[(2-isopropyl-4-thiazolyl)methyl]amino]carbonyl]valinyl]amino]-1,6-diphenyl-3-hydroxyhexane In a 5.0 L reactor equipped with stirrer system and under $N_2$ atmosphere, add a solution containing the product of the example 1B in chloroform (2.5 L) and a solution of N—[[N-methyl-N-[(2-isopropyl-4-thiazolyl)methyl]amino]carbonyl]L-valinyl hydroxysuccinimide ester (107 g, 0.26 mol) in chloroform (630 mL). Keep the system under stirring and monitor the reaction by TLC. At the end of the reaction add a solution of sodium carbonate (100, 1.9 L), separate and dry the organic phase with sodium sulfate. After evaporating the solvent, under reduced pressure, add to the crude product ethyl acetate (1.9 L). Filter under vacuum the crystallized white solid and dry it in an oven at 40° C. Yield: 205 g.

RMN-$^1$H (500 MHz, CDCl$_3$) δ 0.83 (d, J=6.9 Hz, 3H); 0.85 (d, J=6.7 Hz, 3H); 0.89 (d, J=6.5 Hz, 3H); 0.90 (d, J=6.7 Hz, 3H); 1.36 (d, J=6.9 Hz, 6H); 1.37 (d, J=6.8 Hz, 6H); 1.56-1.66 (m, 2H); 2.06-2.14 (m, J=6.7 Hz, 1H); 2.16-2.26 (m, J=6.6 Hz, 1H); 2.71 (dd, J=6.7 e 14.0 Hz, 1H); 2.75 (dd, J=6.8 e 14.0 Hz, 1H); 2.81 (dd, J=7.6 e 13.7 Hz, 1H); 2.86 (dd, J=7.4 e 13.6 Hz, 1H); 2.97 (s, 6H); 3.261 (m, J=6.9 Hz, 1H); 3.263 (m, J=6.9 Hz, 1H); 3.62-3.70 (m, 1H); 3.98-4.10 (m, 3H); 4.16-4.26 (m, 1H); 4.36-4.48 (m, 4H); 4.48-4.52 (m, 1, 1H); 5.94-6.04 (m, 1, 1H); 6.10-6.18 (m, 1, 1H); 6.67 (d, J=8.3 Hz, 1H); 6.75 (d, J=8.1 Hz, 1H); 6.94 (s, 1H); 6.98 (s, 1H); 7.02-7.06 (m, 2H); 7.06-7.12 (m, 4H); 7.12-7.20 (m, 4H).

RMN-$^{13}$C (125.7 MHz, CDCl$_3$): δ 17.7; 18.0; 19.6; 19.6; 23.0; 23.1; 23.2; 29.8; 30.4; 33.2; 34.9; 34.9; 38.3; 39.8; 41.3; 49.1; 49.1; 49.2; 55.2; 60.3; 60.4; 69.4; 113.9; 114.1; 126.0; 126.2; 128.1; 129.2; 129.3; 137.7; 138.4; 151.9; 152.0; 158.5; 158.9; 172.2; 178.9; 179.1.

Melting range: 180-185° C.

$[\alpha]_D^{25}$=−26.3° (C=1%, chloroform)

Example 2

Preparation of the compound (2S,3S,5S)-2-[N—[N [[N-methyl-N-[(2-isopropyl-4-thiazolyl)methyl] amino]carbonyl]vanilyl]amino]-5-(N-((5-thiazolyl) methoxycarbonyl)amino)-1,6-diphenyl-3-hydroxyhexane.

In a 4.0 L reactor equipped with stirrer system and under $N_2$ atmosphere, add a solution containing the compound obtained in the example 1B in THF (2.9 L) and (N-(5-thiazolyl)methyl)-(4-nitrophenyl) carbonate (76 g, 0.27 mol). Keep the reaction under stirring at ambient temperature monitoring the reaction by TLC. Remove the solvent under reduced pressure, dissolve the crude product with ethyl acetate (2.0 L), wash the organic phase with 1N sodium hydroxide solution (8×500 mL) and saturated sodium chloride solution, and dry with sodium sulfate. Concentrate the product under reduced pressure until it achieves ⅓ of the volume and then crystallize the product adding hexane. Dry the white solid in an oven at 40° C. Yield: 141 g.

RMN-$^1$H (500 MHz, CDCl$_3$): δ 0.85 (d, J=6.8 Hz, 3H); 0.88 (d, J=6.8 Hz, 3H); 1.36 (d, J=6.8 Hz, 6H); 1.58-1.72 (m, 2H); 2.11 (m, J=7.0 Hz, 1H); 2.76 (d, J=6.0 Hz, 2H); 2.88 (d, J=7.4 Hz, 2H); 2.91 (s, 3H); 3.26 (m, J=7.0 Hz, 1H); 3.72-3.82 (m, 1, 1H); 3.96-4.08 (m, 1H); 3.98 (t, J=7.4 Hz, 1H); 4.11 (q, J=8.0 Hz, 1H); 4.36 (d, J=16.1 Hz, 1H); 4.41 (d, J=16.1 Hz, 1H); 5.15 (d, J=13.0 Hz, 1H); 5.20 (d, J=13.3 Hz, 1H); 5.56 (d, J=8.4 Hz, 1H); 6.04-6.24 (m, 1, 1H); 6.94 (s,

1H); 6.96 (s, 1H); 6.96-6.99 (m, 1, 1H); 7.00-7.20 (m, 2H); 7.20-7.21 (m, 8H); 7.77 (s, 1H); 8.74 (s, 1H).

RMN-$^{13}$C (125.7 MHz, CDCl$_3$): δ 18.1; 19.6; 23.0; 23.1; 30.0; 33.1; 34.8; 38.2; 38.7; 41.1; 49.1; 50.6; 54.5; 57.8; 60.9; 69.7; 114.2; 126.0; 126.2; 128.1; 128.2; 129.2; 129.4; 133.5; 137.6; 138.4; 143.1; 151.7; 154.4; 155.4; 158.7; 172.3; 179.1.

Example 3

Preparation of the compound (2S,3S,5S)-2,5-bis(N-((5-thiazolyl)methoxycarbonyl)amino)-1,6-diphenyl-3-hydroxyhexane.

A. (2S,3S,5S)-2-(N-((5-thiazolyl)methoxycarbonyl)amino)-5-(t-butyloxycarbonylamine)-1,6-diphenyl-3-hydroxyhexane In a 6.0 L round flask equipped with stirrer system and under N$_2$ atmosphere, add a solution containing (2S,3S,5S)-2-amino-3-hydroxyl-5-(t-butyloxycarbonylamine)-1,6-diphenyl hexane (100 g, 0.26 mol) in THF (1.9 L) and a solution containing (N-(5-thiazolyl)methyl)-(4-nitrophenyl) carbonate (76 g, 0.27 mol) in THF (630 mL). Monitor the reaction by thin layer chromatography, remove the solvent under reduced pressure, dissolve the crude product with ethyl acetate (2.0 L), wash the organic phase using 1N sodium hydroxide solution (8×500 mL) and saturated sodium chloride solution, and dry the product with sodium sulfate. Separate the phases, concentrate the crude product and employ it directly in the next step without previous purification.

B. (2S,3S,5S)-2-(N-((5-thiazolyl)methoxycarbonyl)amino)-5-amino-1,6-diphenyl-3-hydroxyhexane In a 3.5 L round flask, equipped with stirrer system, add a solution containing the product obtained in the example 3A in chloroform (1.4 L), then add slowly concentrated hydrogen chloride (36.9 mL) and distilled water (550 mL). Monitor the reaction by TLC and then, at the end of the reaction, add 820 mL of 10% sodium carbonate solution. Keep the system under stirring until complete dissolution of the solids, separate the phases, wash the organic phase with 10% sodium carbonate solution (3×820 mL) and dry using magnesium sulfate. Concentrate the product under reduced pressure and employ the crude product directly in the next step without previous purification.

C. (2S,3S,5S)2,5-bis-(N-((5-thiazolyl)methoxycarbonyl)amino)1,6-diphenyl-3-hydroxyhexane In a 3.0 L round flask, equipped with stirrer system and under N$_2$ atmosphere, add a solution containing the product obtained in the example 3B in THF (1.9 L). Keep the mixture under stirring and add a solution containing (N-(5-thiazolyl) methyl)-(4-nitrophenyl) (76 g, 0.27 mol) in THF (630 mL). Monitor the reaction by thin layer chromatography, remove the solvent under reduced pressure, dissolve the crude product with ethyl acetate (2.0 L), wash the organic phase using 1N sodium hydroxide solution (8×500 mL) and saturated sodium chloride solution, and dry using sodium sulfate. Concentrate the product under reduced pressure until it achieves ⅓ of the total volume and, then, recrystallize the product by addition of hexane. Dry the white solid in an oven at 40° C. Yield: 111 g.

IV (KBr, cm$^{-1}$): 3376; 3316; 3264; 3052; 3024; 2924; 2860; 2788; 1704; 1552; 1545; 1496; 1456; 1396; 1352; 1288; 1248; 1192; 1124; 1048; 1004; 964; 876; 808; 756; 704; 616; 596.

RMN-$^1$H (Brucker, 500 MHz, DMSO-d$_6$): δ 1.49 (t, J=7.0 Hz, 2H); 2.56 (dd, J=9.2 e 13.7 Hz, 1H); 2.62-2.78 (m, 3H); 3.52-3.60 (m, 1H); 3.84-3.98 (m, 2H); 4.35 (d, J=6.3 Hz, 1H); 5.09-5.24 (m, 4H, AA'); 6.92 (d, J=9.4 Hz, 1H); 7.04-7.26 (m, 11H); 7.86 (s, 2H); 9.04 (s, 1H); 9.06 (s, 1H)

RMN-$^{13}$C (125.7 MHz, DMSO-d$_5$): δ 37.0; 39.0; 39.9; 49.3; 55.3; 56.9; 57.1; 68.7; 125.7; 125.7; 127.8; 127.9; 128.9; 129.0; 134.0; 134.1; 138.9; 139.4; 142.9; 142.9; 155.0; 155.3; 155.4; 156.0.

Example 4

Alternative process for preparation the compound (2S,3S,5S)-2,5-bis[N—[N—[[N-methyl-N-[(2-isopropyl-4-thiazolyl)methyl]amino]carbonyl]valinyl]amino]-1,6-diphenyl-3-hydroxyhexane A. (2S,3S,5S)-2-[N—[N—[[N-methyl-N-[(2-isopropyl-4-thiazolyl)methyl]amino]carbonyl]valinyl]amino]-5-(t-butyloxycarbonylamine)-1,6-diphenyl-3-hydroxyhexane In a 2.5 L reactor with stirrer system and under N$_2$ atmosphere, add N—[[N-methyl-N[(2-isopropyl-4-thiazolyl)methyl]amino]carbonyl]L-valine (98 g, 0.32 mol), 1-hydroxybenzotriazol monohydrate and THF (1.7 L). After complete dissolution of the solids add N,N-dicyclohexylcarbodiimide (76 g, 0.37 mol) in a single portion. Monitor the reaction by TLC, and then filter the mixture to remove dicyclohexylurea precipitate. In a 5.0 L reactor, with stirring and under N$_2$ atmosphere, add (2S,3S,5S)-2-amino-3-hydroxy-5-(t-butyloxycarbonylamine)-1,6-diphenyl hexane (100 g, 0.26 mol), THF (1.9 L) and the solution containing the activate derivative ester HOBt prepared as above mentioned. Monitor the reaction by thin layer chromatography and, at the end of the reaction, concentrate the mixture under reduced pressure, then dilute it with ethyl acetate (1.0 L). Wash it using saturated sodium bicarbonate solution and saturated sodium chloride solution, then concentrate the product under reduced pressure and dilute it with chloroform (1.9 L). Employ this chloroform solution directly in the next step.

B. (2S,3S,5S)-2-[N—[N—[[N-methyl-N-[(2-isopropyl-4-thiazolyl)methyl]amino]carbonyl]valynil]amino]-5-amino-1,6-diphenyl-3-hydroxhexane In a 5.0 L reactor, equipped with an addition funnel and stirrer system, add the solution obtained in the step A (~1.9 L). Keep the system under stirring, add slowly concentrated hydrogen chloride (154 mL) monitoring the reaction by thin layer chromatograph. After reaction finishes, as indicated by TLC, add water (1.0 L), separate the phases and adjust the aqueous phase pH to 9 using 10% sodium carbonate solution. Extract aqueous phase using chloroform (3×640 mL) and dry the organic phase under reduced pressure, dilute the crude product with THF (1.9 L) and employ the final solution directly in the next step.

C. (2S,3S,5S)-2,5-bis-[N—[N—[[N-methyl-N-[(2-isopropyl-4-thiazolyl)methyl]amino]carbonyl]vanilyl]amino]-1,6-diphenyl-3-hydroxyhexane In a 2.5 L reactor with a stirrer system and under an N$_2$ atmosphere, add N—[[N-methyl-N-[(2-isopropyl-4-thiazolyl)methyl]amino]carbonyl]L-valine (98 g, 0.32 mol), 1-hydroxybenzotriazol monohydrate and THF (1.7 L). After complete dissolution of the solids, add N,N-dicyclohexylcarbodiimide (76 g, 0.37 mol) in a single portion. Monitor the reaction by TLC and, at the end of the reaction, filter the mixture to remove dicyclohexylurea precipitate. Add the resultant solution to the solution obtained in the step B (5.0 L reactor, with stirring under $N_2$ atmosphere). Keep the system under stirring monitoring the reaction by TLC. At the end of the reaction, concentrate the mixture under reduced pressure and then dilute it with chloroform (1.9 L). Wash with saturated sodium bicarbonate solution and saturated sodium chloride solution. Concentrate the crude organic phase under reduced pressure and add ethyl acetate (1.9 L) to the crude product. Filter the white solid under vacuum and dry it in an oven at 40° C. Yield: 206 g.

RMN-$^1$H (500 MHz, CDCl$_3$) δ 0.83 (d, J=6.9 Hz, 3H); 0.85 (d, J=6.7 Hz, 3H); 0.89 (d, J=6.5 Hz, 3H); 0.90 (d, J=6.7 Hz, 3H); 1.36 (d, J=6.9 Hz, 6H); 1.37 (d, J=6.8 Hz, 6H); 1.56-1.66 (m, 2H); 2.06-2.14 (m, J=6.7 Hz, 1H); 2.16-2.26 (m, J=6.6 Hz, 1H); 2.71 (dd, J=6.7 e 14.0 Hz, 1H); 2.75 (dd, J=6.8 e 14.0 Hz, 1H); 2.81 (dd, J=7.6 e 13.7 Hz, 1H); 2.86 (dd, J=7.4 e 13.6 Hz, 1H); 2.97 (s, 6H); 3.261 (m, J=6.9 Hz, 1H); 3.263 (m, J=6.9 Hz, 1H); 3.62-3.70 (m, 1H); 3.98-4.10 (m, 3H); 4.16-4.26 (m, 1H); 4.36-4.48 (m, 4H); 4.48-4.52 (m, 1, 1H); 5.94-6.04 (m, 1, 1H); 6.10-6.18 (m, 1, 1H); 6.67 (d, J=8.3 Hz, 1H); 6.75 (d, J=8.1 Hz, 1H); 6.94 (s, 1H); 6.98 (s, 1H); 7.02-7.06 (m, 2H); 7.06-7.12 (m, 4H); 7.12-7.20 (m, 4H).

RMN-$^{13}$C (125,7 MHz, CDCl$_3$): δ 17.7; 18.0; 19.6; 19.6; 23.0; 23.1; 23.2; 29.8; 30.4; 33.2; 34.9; 34.9; 38.3; 39.8; 41.3; 49.1; 49.1; 49.2; 55.2; 60.3; 60.4; 69.4; 113.9; 114.1; 126.0; 126.2; 128.1; 129.2; 129.3; 137.7; 138.4; 151.9; 152.0; 158.5; 158.9; 172.2; 178.9; 179.1.

Melting range: 180-185° C.

$[α]_D^{25}$=−26.3° (C=1%, chloroform)

Example 5

Antiviral Activity

The anti-HIV activity of the compound of the present invention was determined using MT-4 cells, a lymphocytic cell line established in culture, CD4$^+$, and expressing HIV-1 C5 and R4 co-receptors. The cells were infected using a plate having 96 wells containing 10$^4$ cells/well. The cells were infected with MOI (Multiplicity Of Infection) of 0.002 (NIH requirement=0.001 to 0.01). The drugs were initially diluted in dimethyl sulfoxide (DMSO) to a final concentration of 20 mM and later in RPMI 1640 base medium to a concentration of 200 μM. Eight wells containing cells previously infected with isolated HIV pNL4-3 (subtype B) were exposed to gradually decreased concentrations of the drug starting from 10 μM using a dilution factor of 5. The culture medium utilized for this procedure was RPMI 1640 including 10% bovine fetal serum, antibiotics streptavidin/penicillin and L-glutamine. The most concentrated well has a final concentration of 10.000 μM being followed by the indicated dilutions: 2.0 μM; 0.400 μM; 0.0800 μM; 0.016 μM; 0.0032 μM; 0.00064 μM and 0.000128 μM. The ninth well is considered as the infection control, without adding the drug. Each line having 10 infected wells is produced in triplicate for later statistics analyses. The fourth cell line (containing 10 wells) is exposed to the serial dilution of the drug as described above, but with no inoculation of the virus, for analysis of drug cytotoxicity at this concentration range.

The infection test is maintained in an incubator having 5% of $CO_2$ at 37° C. and monitored daily using phase optical microscopy method to verify appearance of syncytia (multinuclear cells). Generally, it happens after the fourth day of the infection. Staining with 3-(4,5-dimethylthiazol-2-yl)-2,5-diphenyltetrazolium bromide (MTT) [Hertogs, K et al., *Antimicrob. Agents Chemoter.*, 42(2), 269-275, 1998] was performed at the sixth day in order to allow the determination of cellular viability after formation of the syncytia. After staining, the 96 well plate is scanned in ELISA equipment having a 490 nm absorption filter. The values were appraised in a Microsoft Excel for Windows (Office 98) spreadsheet, then corrected for the blank and the data are graphed (in percentage, using as standard the vessel containing viable cells with no infection having 100% of emission) as the cellular viability measure. The point indicating 50% of the standard emission was considered the "cutoff" value to calculate $EC_{50}$ (concentration of the drug that causes the inhibition of 50% of the infection) that is obtained in the equation of the logarithmic regression curve (or semi-logarithmic).

Figure 2:
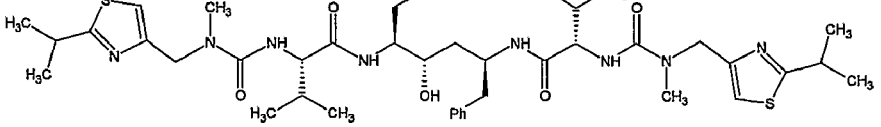
FIG. 2 presents the $EC_{50}$ values obtained for each analogous compound of the ritonavir together with the value obtained for ritonavir used as internal control assay.
Figure 2:
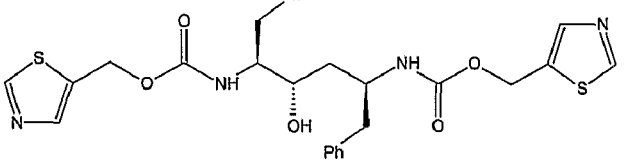
Figure 2:
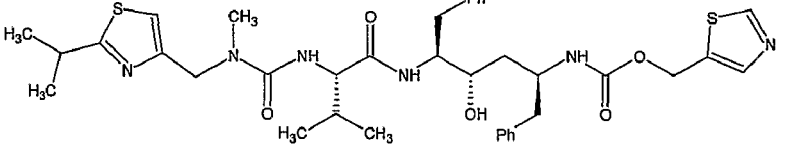
Figure 2:
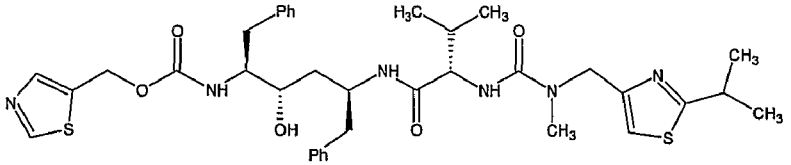

FIG. 2 presents the $EC_{50}$ values obtained for each analogous compound of the ritonavir together with the value obtained for ritonavir used as internal control assay.

The results of the antiviral activity tests displayed in FIG. 2 demonstrate that a preferred compound of the present invention (example 1C) presents a surprisingly superior activity not only in comparison with ritonavir and analogs thereof synthesized by us, but also in comparison with the other analogous compounds described in the art having their anti-HIV activity already determined.

The compound of the present invention is useful to inhibit retroviral protease, particularly HIV protease, in vitro or in vivo.

The compound of the present invention can be administered to an individual for prophylaxis and/or treatment of disease caused by a retrovirus, especially acquired immunodeficiency syndrome or an HIV infection, in a therapeutically effective amount for this treatment. The term "individual" used herein preferably includes human but also can refer to animals, especially mammals. The term "therapeutically effective amount" is used herein referring to the amount of the compound analogous to ritonavir, in the form of free base or salt, ester or prodrug thereof that causes the desired medical or biological response.

The total daily dose administered to an human or other mammal in a single dose or divided along the day can be in an amount of, for instance, 0.001 to 300 mg/Kg (per body weight) and, more usually 0.1 to 10 mg. The active ingredient amount can be combined with suitable pharmaceutical excipients to produce a dosage form and varies depending on general health state of the patient and the adopted form of administration.

The compound of the present invention can be administered to individuals via conventional administration routes including, but not limited to oral, intravenous, subcutaneous, intramuscular, nasal, transdermal, and topical, among others. Preferably, the administration route is oral with the purpose of increase the predisposition of the individuals to the treatment.

The compound of the present invention can be formulated in the form of pharmaceutical compositions suitable to the administration route selected. Therefore, this compound can be formulated in the form of pills, capsules, tablets, powders, granules, aerosols, elixirs, solutions, suspensions, emulsions, syrups, etc.

Solid pharmaceutical compositions suitable for oral administration include capsules, tablets, pills, powders and granules. For preparation of solid pharmaceutical composition such as tablets or capsules, the active compound is mixed with suitable pharmaceutical excipients such as starch, lactose, sucrose, sorbitol, stearic acid, magnesium stearate, among others, also including other pharmaceutical diluents such as water or an organic solvent, to form an homogeneous composition. Additionally, tablets and pills can be prepared with an enteric coating which protects the medication against an undesirable degradation in the stomach allowing its release into duodenum.

Liquid pharmaceutical compositions suitable for oral administration include, for instance, solutions, suspensions, emulsions, syrups and elixirs containing diluents commonly used in the art such as water and other excipients such as moisturizing agents, emulsifying and dispersing agents, sweeteners and flavoring agents and stabilizing agents.

The compound of the present invention can be administered as a single active ingredient but also can be used in combination with other anti-HIV drugs. When it is administered in combination, the active ingredients can be formulated as separated compositions that are administered simultaneously or at different periods, or the active ingredients can be administered in a common pharmaceutical composition.

The invention claimed is:
1. A compound of the formula:

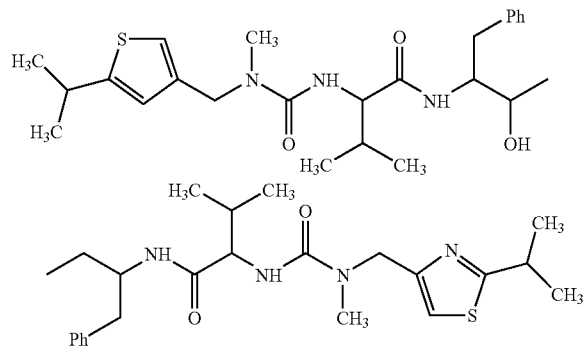

or a pharmaceutically acceptable salt, ester or prodrug thereof, wherein Ph is a phenyl group.

2. The compound (2S,3S,5S)-2,5-bis-[N—[N—[[N-methyl-N-[(2-isopropyl-4-thiazolyl)methyl]amino]carbonyl]valinyl]amino]-1,6-diphenyl-3-hydroxyhexane, or a pharmaceutically acceptable salt, ester or prodrug thereof.

3. A process to prepare the compound (2S,3S,5S)-2,5-Ns-[N—[N—[[N-methyl-N-[(2-isopropyl-4-thiazolyl)methyl]amino]carbonyl]valinyl]amino]-1,6-diphenyl-3-hydroxyhexane which comprises reacting (2S,3S,5S)-2-[N—[N—[[N-methyl-N-[(2-isopropyl-4-thiazolyl)methyl]amino]carbonyl]valinyl]amino]-5-amino-3-hydroxy-1,6-diphenyl hexane with N—[[N-methyl-N-[(2-isopropyl-4-thiazolyl)methyl]amino]carbonyl]L-valinyl hydroxy-succinimide ester.

4. A pharmaceutical composition comprising a suitable pharmaceutical excipient and a therapeutically effective amount of the compound (2S,3S,5S)-2,5-bis-[N—[N—[[N-methyl-N-[(2-isopropyl-4-thiazolyl)methyl]amino]carbonyl]valinyl]amino]-1,6-diphenyl-3-hydroxyhexane, or a pharmaceutically acceptable salt, ester or prodrug thereof.

5. A method for treating an HIV infection which comprises administering a therapeutically effective amount of (2S,3S,5S)-2,5-his-[N—[N—[[N-methyl-N-[(2-isopropyl-4-thiazolyl)methyl]amino]carbonyl]valinyl]amino]1,β-diphenyl-3-hydroxyhexane or a pharmaceutically acceptable salt, ester or prodrug thereof, in combination with a therapeutically effective amount of another HIV protease inhibitor compound, to a patient needing treatment.

6. A method for treating an HIV infection which comprises administering a therapeutically effective amount of (2S,3S,5S)-2,5-bis-[N—[N—[[N-methyl-N-[(2-isopropyl-4-thiazolyl)methyl]amino]carbonyl]vanilyl]amino]-1,6-diphenyl-3-hydroxyhexane or a pharmaceutically acceptable salt, ester or prodrug thereof in combination with a therapeutically effective amount of a reverse transcriptase inhibitor compound, to a patient needing treatment.

* * * * *